United States Patent [19]

McEntire

[11] 4,256,666

[45] Mar. 17, 1981

[54] PREPARATION OF β-AMINOPROPIONAMIDES

[75] Inventor: Edward E. McEntire, Austin, Tex.

[73] Assignee: Texaco Development Corporation, White Plains, N.Y.

[21] Appl. No.: 89,061

[22] Filed: Oct. 29, 1979

[51] Int. Cl.³ .................................... C07C 102/06
[52] U.S. Cl. ......................... 564/135; 260/326.25; 544/56; 544/96; 546/186; 546/208; 546/209; 564/197
[58] Field of Search .......... 260/561 A, 561 R, 326.25; 546/186, 208, 209; 544/86, 96

[56] References Cited

U.S. PATENT DOCUMENTS

| | | | |
|---|---|---|---|
| 2,451,436 | 10/1948 | Erickson | 260/561 N |
| 3,145,195 | 8/1964 | Tsou | 260/561 A |
| 3,912,780 | 10/1975 | Ribka et al. | 260/561 N |
| 3,924,046 | 12/1975 | Ribka et al. | 260/561 N |
| 4,031,138 | 6/1977 | Nieh et al. | 260/561 N |
| 4,134,916 | 1/1979 | Moss et al. | 260/561 N |

*Primary Examiner*—Arthur P. Demers
*Attorney, Agent, or Firm*—Carl G. Ries; Robert A. Kulason; James L. Bailey

[57] ABSTRACT

Covers a process for the preparation of a β-aminopropionamide of the formula

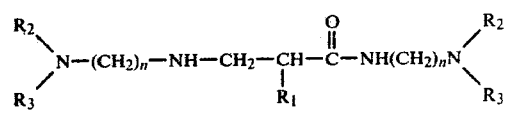

wherein $R_1$ is H or methyl, n is an integer of 2 to 6 and $R_2$ and $R_3$, taken singly are hydrogen or lower alkyl groups containing 1 to 4 carbon atoms or $R_2$ and $R_3$, taken jointly are combined with the nitrogen atom to form a heterocyclic group selected from the groups consisting of morpholine, pyrrolidine and piperidine ring groups; which process comprises reacting in the presence of a Lanthanide salt having an anion derivative from a strong acid having a $pK_a$ of about 5 or less acting as a catalyst, a tertiaryaminoalkyl amine of the formula:

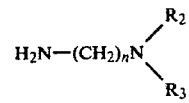

where $R_2$, $R_3$ and n are as above with an acrylic or methacrylic compound of the formula:

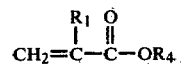

where $R_1$ is as above and $R_4$ is lower alkyl and recovering said β-aminopropionamide.

9 Claims, No Drawings

PREPARATION OF β-AMINOPROPIONAMIDES

BACKGROUND OF THE INVENTION

1. Field of the Invention

The present invention relates to a catalytic chemical process for making β-aminopropionamides. Such compounds are particularly useful derivatives in further preparing cationic vinyl monomers useful in preparing flocculants, adhesion promoters, oil soluble dispersions, epoxy curing agents and ion exchange resins.

2. Description of the Prior Art

It is well-known that amines will react with acrylic or methacrylic esters to form β-aminopropionamides. Thus, for example, certain β-aminopropionamides compounds can be made by reacting dialkyl amine compounds with an acrylic acid or ester compound, as described in the article by J. G. Erickson, "The Preparation and Stabilities of Some β-dialkylaminopropionamides", J. Am. Chem. Soc. 74, 6281-82 (1952).

Aminolysis of esters is also described by J. F. Bunnett and G. T. Davis, J. Am. Chem. Soc. 82, 665 (1960) and H. T. Openshaw and M. Whittaker, J. Chem. Soc. 89, (1969). Other processes leading to compounds of this type are set out in U.S. Pat. Nos. 2,451,436; 2,529,838; 2,649,438; and 3,652,671.

As set out in U.S. Pat. Nos. 2,719,175 and 2,719,178 the resultant β-aminopropionamides can then be broken down by heat to give monomeric compounds.

Other work of this type is described by H. L. Bassett and C. R. Thomas, J. Chem. Soc. 1188 (1954) in German Pat. No. 1,164,397.

However, normally the reaction between an amine and an acrylic or methacrylic ester will proceed only slowly at moderate temperatures. One can elevate the temperature to complete the reaction and form the desired propionamide but then side reactions become significant.

In order to promote the reactions between esters and amines use of certain compounds have been suggested. For example, in the article by H. L. Bassett and C. R. Thomas, J. Chem. Soc. 11, 1188 (1954) the use of stoichiometric quantities of an alkylmagnesium halide has been described. While such compounds have been found to act as an aid in forming amides, it was also found that catalytic quantities were not effective here. In yet another route in producing acrylamides from acrylic esters and amides the use of lithium hydroxide and magnesium methoxide as catalysts were proposed (German Pat. No. 1,164,397).

However to date no simple method has been found to form β-aminopropionamides from acrylic or methacrylic esters and the appropriate amines, which can be run at relatively low reaction temperatures, and which results in few side products compared to the prior art. Some catalysts, for example, in this area may catalyze the desired reaction, and likewise promote undesired side reactions.

It would therefore be an advantage in the art to provide a new catalytic method for preparing β-aminopropionamides, which reaction could be run at relatively low reaction temperature and would produce few quantities of undesired side products.

SUMMARY OF THE INVENTION

The present invention is an improved catalytic process for the preparation of β-aminopropionamides of the formula:

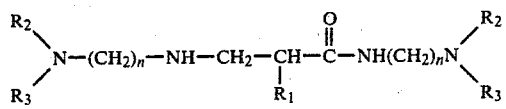

wherein $R_1$ is H or methyl, n is an integer of 2 to 6 and $R_2$ and $R_3$, taken singly are hydrogen or lower alkyl groups containing 1 to 4 carbon atoms or $R_2$ and $R_3$, taken jointly when combined with the nitrogen atom form a heterocyclic group selected from the group consisting of morpholine, pyrollidine and piperidine ring groups; which process comprises reacting in the presence of a Lanthanide salt having an anion derived from a strong acid having a $pK_a$ of about 5 or less of the acting as a catalyst, a tertiaryaminoalkyl amine of the formula.

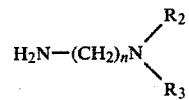

where $R_2$, $R_3$ and n are as above with an acrylic or methacrylic compound of the formula:

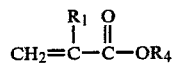

where $R_1$ is as above and $R_4$ is lower alkyl and recovering said β-aminopropionamide.

DETAILED DESCRIPTION OF THE INVENTION

The inventive process can be carried out batchwise or in a substantially continuous procedure. Usually a molar excess of a tertiary-aminoalkylamine is combined with the acrylic or methacrylic acid ester compound, and the mixture is heated at a temperature within the range of 20°–200° C., most preferably 60°–140° C.

Most often at least two moles of the amine are utilized per mole of ester, and more often to drive the reaction to completion an excess greater than two moles of amine is employed. This insures maximum formation of the corresponding β-aminopropionamide compound. There is no criticality in the maximum amount of amine compound employed other than practical considerations of subsequent excess unreacted amine removal from the reaction mixture. Normally, the reaction product is formed within a time period of about ¼ to 24 hours, more often 0.5–10 hours. The amount of reaction time depends upon the particular starting materials employed and temperatures employed. The corresponding β-aminopropionamide reaction product can then be separated from the reaction mixture, which usually also contains alcohols and excess unreacted amine compound, if desired, by conventional distillation procedures. However, the inventive process is equally applicable to the continuous running of the entire reaction mixture, for the alcohol of reaction and excess unreacted amine do not adversely effect the process.

The reaction may also be effected at atmospheric, subatmospheric or superatmospheric pressures. Usually the reaction is run at a pressure range slightly greater than 1 atmosphere.

Tertiary aminoalkylamines which are especially useful in the practice of the present invention include: 3-dimethylaminopropylamine; 2-dibutylaminoethylamine; 4-(aminopropyl)morpholine; 3-diethylaminopropylamine; 2-dimethylaminoethylamine; 1-(aminopropyl)piperidine; and 4-(aminoethyl)-morpholine. Most preferably, 3-dimethylaminopropylamine is employed.

$R_2$ and $R_3$ when lower alkyl are most preferable $C_1$-$C_4$ lower alkyl such as isopropyl and t-butyl and can also contain other substituents of the non-interfering type such as halo, aryl, nitro, alkaryl, hindered amines such as tertiary amines and secondary amines, hindered hydroxyl groups, ether linkages, etc. The alkyl group may contain any substituent of this type which is inert to the reaction conditions.

Particular acrylic acid or methacrylic acid ester compounds useful as reactants in the invention include: methyl acrylate, methyl methacrylate, ethyl acrylate, and ethyl methacrylate. Methyl acrylate and methyl methacrylate are preferred.

The amount of catalyst utilized may vary over a wide range. Usually based on the total weight of the reactants a catalyst is used in an amount ranging from about 0.01 up to about 10% by weight. More often the catalyst is employed in the range of 0.1-5 weight % based on total reactant weight present.

Any catalyst salt containing an element of the Lanthanide Series of the Periodic Table including elements numbered 57-71 may be employed. Such compounds of the Lanthanide Series which are suitable catalysts include ionic species where the anion is derived from a strong acid.

Particularly preferred compounds are those containing lanthanum and cerium. Other useful compounds contain europium and ytterbium.

Particularly preferred compounds of the Lanthanide Series, and more particularly lanthanum and cerium include the halides, nitrates, perchlorates and fluoroborates.

The anionic portion of the Lanthanide type compound useful here may be mixed in character; that is, the counteriron may be two or more differing anions, as long as one is the anion of a strong acid. Again, the salt compound may contain two or more differing elements of the Lanthanide Series. Lastly, the anionic portions of the molecule may be organic such as the tosylate ion or inorganic in character.

The following examples are for purposes of illustration of the invention and are not intended to be limiting thereof.

EXAMPLE I

To a 500 cc flask with a stirrer, thermometer and nitrogen atmosphere were charged
  204 g 3-dimethylaminopropylamine (DMAPA)
  8.5 g lanthanum bromide.
The contents of flask (slurry) were heated to 80° C. and 100 g of methyl methacrylate (MMA) was added. Heating at 80° C. was continued for 3 hours, then the reactor contents were sampled. Gas-liquid chromatography of the filtrate showed a 22.6% yield of the desired β-aminopropionamide, and a yield of methanol of 48.7%. Much of the product was the Michael adduct of MMA and DMAPA. The conversion of MMA was ca. 97%.

EXAMPLES 2-7

The following examples were conducted in an identical fashion to Example I, and 0.022 moles of catalyst was used.

| Run No. | Catalyst | Propionamide** % Yield | Methanol % Yield |
|---|---|---|---|
| 2 | none | 0.1 | 1.2 |
| 3 | La(NO$_3$)$_3$—6H$_2$O | 29.0 | 53.6 |
| 4 | Ce$_2$Mg$_3$(NO$_3$)$_{12}$24H$_2$O | 23.3 | 54.7 |
| 5 | Ce(NH$_4$)$_2$(NO$_3$)$_6$ | 36.1 | 78.5 |
| 6 | LaCl$_3$—7H$_2$O | 13.7 | 36.4 |
| 7 | CeI$_3$ | 35.1 | 30.3 |

**Propionamide = N-(3-(dimethylamino)propyl)-3-(3-(dimethylamino)propylamino-2-methylpropionamide. Yield is % of theoretical basis gas liquid chromatography area percent.

By comparing the reactions with the blank run (Example 2) the Examples 3-7 show very active catalysts. Note that Run No. 5 shows that mixed anions may be present in the molecule.

EXAMPLE 8

An experiment identical to Example 3 was performed, except the reaction mixture was heated 6 hours at 85° C. instead of 3 hours at 80° C. Gas liquid chromatography showed higher conversion and yields (83% yield of methanol, 54% yield of propionamide). Thus increased heating time significantly increases production of the propionamide.

EXAMPLES 9-16

The following examples were conducted in an identical fashion to Example 1, and 0.022 moles of catalyst was used.

| Run No. | Catalyst | Propionamide % Yield | Methanol Yield |
|---|---|---|---|
| 9 | YCl$_3$ . 6H$_2$O | 27.0 | 54.3 |
| 10 | Yb(NO$_3$)$_3$ . 5H$_2$O | 21.9 | 49.5 |
| 11 | LaRE(NO$_3$)$_3$ . 6H$_2$O[1] | 24.4 | 37.2 |
| 12 | La(OTs)$_3$ | 10.1 | 9.6 |
| 13 | Nd(NO$_3$)$_3$ . 5H$_2$O | 18.5 | 35.3 |
| 14 | Ce(AcAc)$_3$ . xH$_2$O[3] | 0.2 | 3.8 |
| 15 | La$_2$O$_3$ | 0 | 1.0 |
| 16 | La(OC$_3$H$_7$)$_3$[4] | 0.6 | 17.7 |

[1] LaRE = mixed La, Nd, Ce, Pr, ang other rare earths in the approximate respective weight ratios of 60, 21.5, 10, 7.5, and 1.0, compared on the basis of their oxides.
[2] Ts = toluene sulfonyl
[3] AcAc = acetylacetonate
[4] OC$_3$H$_7$ = isopropoxy Note that Example 11 demonstrates that mixed rare earth compounds are suitable as catalysts. Example 14 through 16 show that lanthanides from weak acids are largely ineffective catalysts.

Obviously, many modifications and variations of the invention as here an before set forth may be made without departing from the spirit and scope thereof, and, therefore, only such limitations should be imposed as indicated in the claims.

The invention is hereby claimed as follows:
1. A process for the preparation of a β-aminopropionamide of the formula

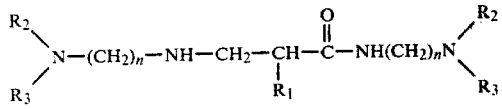

wherein $R_1$ is H or methyl, n is an integer of 2 to 6 and $R_2$ and $R_3$, taken singly are hydrogen or lower alkyl groups or $R_2$ and $R_3$, taken jointly when combined with the nitrogen atom form a heterocyclic group selected from the group consisting of morpholine, pyrrolidine and piperidine ring groups, which process comprises reacting in the presence of a salt of an element of the Lanthanide Series having an anion derived from a strong acid having a $pK_a$ of about 5 or less acting as a catalyst, a tertiaryaminoalkyl amine of the formula:

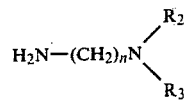

where $R_2$, $R_3$ and n are as above with an acrylic or methacrylic compound of the formula:

$$CH_2=\overset{R_1}{\underset{|}{C}}-\overset{O}{\underset{\|}{C}}-OR_4$$

where $R_1$ is as above and $R_4$ is lower alkyl and recovering said β-aminopropionamide.

2. The process of claim 1 where $R_2$ and $R_3$ are methyl.
3. The process of claim 2 where n=3.
4. The process of claim 3 where $R_1$ is methyl.
5. The process of claim 4 where $R_4$ is methyl.
6. The process of claim 1 which is run at a temperature of 20°–200° C.
7. The process of claim 1 wherein said temperature range is 60°–140° C.
8. The process of claim 1 wherein said catalyst is a lanthanum compound.
9. The process of claim 1 wherein said catalyst is a cerium compound.